United States Patent [19]

Anderson et al.

[11] Patent Number: 4,537,777
[45] Date of Patent: Aug. 27, 1985

[54] A52688 ANTIBIOTICS AND PROCESS FOR THEIR PRODUCTION

[75] Inventors: Marie T. Anderson; Karl H. Michel, both of Indianapolis; Thomas H. Sands, Brownsburg, all of Ind.

[73] Assignee: Eli Lilly and Company, Indianapolis, Ind.

[21] Appl. No.: 562,256

[22] Filed: Dec. 16, 1983

[51] Int. Cl.³ .................... A01N 37/34; C07C 119/02; C12P 13/00
[52] U.S. Cl. .................................. 514/521; 260/464; 260/465 D; 435/128
[58] Field of Search .......................... 260/464, 465 D; 424/304; 435/128

[56] References Cited

PUBLICATIONS

"J. Berdy, CRC Handbook of Antibiotic Compounds", vol. VI, CRC Press, Boca Raton, Fla., pp. 273-274.
A. Takatsuki et al., "New Antiviral Antibiotics; Xanthocillin X Mono- and Dimethylether, and Methoxyxanthocillin X Dimethylether, I. Isolation and Characterization", J. Antibiotics, vol. XXI, 671-675, (1968).
T. Korzybski et al., "Antibiotics: Origin, Nature and Properties", vol. II, Pergamon Press, New York, 1967, pp. 1256-1257.
I. T. Harrison, et al., "Antibacterial Activity of N-(-B-Styryl)formamides Related to Tuberin", J. Med. Chem. 21 (6), 588-591, (1978).
Centraalbureau Voor Schimmelcultures Baarn, "List of Cultures", 29th ed., 1978, p. 184.

Primary Examiner—Dolph H. Torrence

[57] ABSTRACT

New A52688 factors A, C, D, E, F, G, H, J and K which have the common general formula:

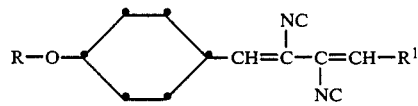

are antibacterial and antineoplastic agents. Methods of preparing the antibiotics by culturing a strain of Mycoleptodiscus terrestris are provided.

40 Claims, No Drawings

A52688 ANTIBIOTICS AND PROCESS FOR THEIR PRODUCTION

SUMMARY OF THE INVENTION

This invention relates to a new group of antibiotics, the A52688 complex. The A52688 complex contains at least ten factors, one of which is an analog of tuberin. The nine new A52688 factors (A, C, D, E, F, G, H, J and K) have the structures shown in formulas 1 through 9.

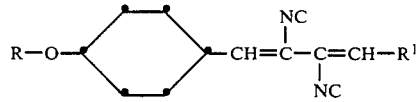

| Formula | Factor | R | R¹ |
|---|---|---|---|
| 1 | A | (CH₃)₂C=CH—C(=O)— | 3,4-dihydroxyphenyl (trans) |
| 2 | C | H | 3,4-dihydroxyphenyl (trans) |
| 3 | D | (CH₃)₂C=CH—C(=O)— | 4-hydroxyphenyl |
| 4 | E | " | 3,4-dihydroxyphenyl (cis) |
| 5 | F | " | 4-acetoxy, =O |
| 6 | G | " | 4-acetoxy, hydroxy |
| 7 | H | " | O—C(=O)—CH₃, OH (trans) |
| 8 | J | " | O—CH₃, OH (cis) |
| 9 | K | (CH₃)₂CHCH₂C(=O)— | 4-acetoxy, OH |

The A52688 antibiotic complex is produced by culturing a strain of *Mycoleptodiscus terrestris* under submerged aerobic fermentation conditions until a substantial level of antibiotic activity is produced. The A52688 antibiotic complex is extracted from the fermentation medium with polar organic solvents and is separated into its individual factors by the use of chromatography.

The A52688 factors are useful as antibiotics and as antitumor agents. Methods of preparing the A52688 antibiotics from *M. terrestris*, methods of treatment and pharmaceutical compositions are also provided by this invention.

DETAILED DESCRIPTION

This invention relates to new compounds which are antibiotics and antitumor agents. In particular, this invention relates to a group of compounds which have been designated as A52688 factors and to methods of treating certain tumors with, and pharmaceutical compositions comprising, these compounds.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentration, longer body half life, and more advantageous rate or route of excretion and rate or pattern of metabolism) are some of the goals for improved antibiotics.

There is also a great need for new, improved antitumor agents. The currently used antitumor agents often have severe negative side effects. In addition, it is frequently necessary to administer several agents in conjunction to achieve maximum antitumor effect. Increased in vivo efficacy and expanded spectrum of tumor inhibition are qualities being sought in antitumor agents.

The A52688 factors of this invention are closely related chemically. As many as ten antibiotic factors are recovered from the fermentation and are obtained as a mixture, the A52688 complex. Individual factors A, B, C, D, E, F, G, H, J and K are isolated as individual compounds as hereinafter described.

The term "antibiotic complex" as used in the fermentation art and in this specification refers to a mixture of co-produced individual antibiotic factors. As will be recognized by those familiar with antibiotic production by fermentation, the ratio of individual factors produced in an antibiotic complex will vary, depending on the fermentation conditions used. Presently, factors A and G are the major factors produced.

The A52688 factors A, C, D, E, F, G, H, J and K, the new antibiotics of this invention, are believed to have the structures shown in formulas 1-9, respectively. A52688 factor B is believed to be the known compound having formula 10; thus, it is related to the antibacterial agent tuberin, the structure of which is shown in formula 11:

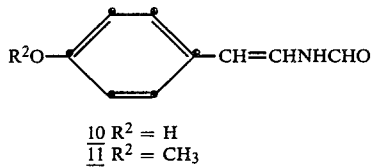

10 $R^2$ = H
11 $R^2$ = $CH_3$

As will be apparent to those skilled in the art, A52688 factors A, C, D, E, G, H, J and K can form monoacyl ester derivatives; factors A, C, and E can form diacyl ester derivatives; and factor C can form a triacyl ester derivative. The pharmaceutically-acceptable acyl esters of factors A, C, D, E, G, H, J and K are also part of this invention. Preferred ester derivatives are those derived from a mono or di-carboxylic acid having from 2 to 18 carbon atoms, such as acetic, butyric, valeric, dodecanoic, phenylacetic, tartaric, maleic, stearic, salicylic, and sorbic acids.

The A52688 complex and factors are soluble in solvents such as dimethyl sulfoxide, dimethylformamide and chloroform, are slightly soluble in solvents such as acetone, methanol, ethyl acetate and acetonitrile, but are insoluble in water and solvents such as hexane.

Table I summarizes certain of the characteristics of the A52688 factors:

TABLE I

| | Characteristics of A52688 Factors | | | |
|---|---|---|---|---|
| Factor | Molecular Weight[a] | Molecular Formula | Corrected mp (°C.) | UV λ max[b] |
| A | 396 | $C_{23}H_{28}N_2O_4$ | 126–127 | 286 nm |
| B | 163 | $C_9H_9NO_2$ | 195–197 | Base-306 nm Acid, neutral- 283 nm |
| C | 314 | $C_{18}H_{22}N_2O_3$ | 128–130 | 286 nm |
| D | 376 | $C_{23}H_{24}N_2O_3$ | 129–131 | Base-383 nm |
| E | 396 | $C_{23}H_{28}N_2O_4$ | 123–124 | Acid, neutral- 328 nm 285 nm |
| F | 436 | $C_{25}H_{28}N_2O_5$ | 93–94 | 220, 248 nm |
| G | 438 | $C_{25}H_{30}N_2O_5$ | 118–119 | Base-288 nm Acid-286 nm Neutral-250 nm |
| H | 438 | $C_{25}H_{30}N_2O_5$ | amorph. | 285 nm |
| J | 410 | $C_{24}H_{30}N_2O_4$ | amorph. | 287 nm |
| K | 440 | $C_{25}H_{32}N_2O_5$ | amorph. | 250 nm |

[a]Determined by mass spectrometry
[b]UV in methanol

The elemental composition of each of the A52688 factors (as an approximate percentage) is summarized in Table II.

TABLE II

| | Elemental Analyses of A52688 Factors | | | | | | | | | |
|---|---|---|---|---|---|---|---|---|---|---|
| | A52688 Factor | | | | | | | | | |
| | A | | B | | C | | D | | E | |
| Element | Calcd. | Found | Calcd. | Found | Calcd. | Found | Calcd. | Found | Calcd. | Found |
| Carbon | 69.67 | 69.86 | 66.26 | 66.19 | 68.79 | 68.58 | 73.40 | 71.35 | 69.70 | 69.76 |
| Hydrogen | 7.12 | 6.77 | 5.52 | 5.39 | 7.01 | 7.27 | 6.38 | 6.15 | 7.07 | 7.32 |
| Nitrogen | 7.07 | 6.79 | 8.59 | 7.88 | 8.92 | 8.69 | 7.45 | 6.79 | 7.07 | 7.27 |
| Oxygen | 16.14 | 16.58 | 19.63 | 20.54 | 15.28 | 15.38 | 12.77 | 14.11 | 16.16 | 15.65 |
| | A52688 Factor | | | | | | | | | |
| | | F | | G | | H | | J | | |
| | Element | Calcd. | Found | Calcd. | Found | Calcd.[a] | Found | Calcd.[a] | Found[b] | |
| | Carbon | 68.81 | 68.83 | 68.49 | 68.68 | 67.11 | 67.81 | 68.74 | 69.10 | |
| | Hydrogen | 6.42 | 6.69 | 6.85 | 7.07 | 6.94 | 6.72 | 7.40 | 6.92 | |
| | Nitrogen | 6.42 | 6.21 | 6.39 | 6.12 | 6.26 | 5.97 | 6.68 | 6.76 | |
| | Oxygen | 18.35 | 18.07 | 18.27 | 18.13 | 19.69 | 19.50 | 17.18 | 17.22 | |

[a]Mol. wt. ½ $H_2O$
[b]Adjusted for presence of 2.43% ash

Table III summarizes the prominent absorptions in the infrared (IR) spectra of the A52688 factors (run in KBr).

TABLE III

| Prominent IR Absorptions in A52688 Factors | |
|---|---|
| Factor | Frequency (cm$^{-1}$)[a] |
| A | 2944, 2861, 2120s, 1701s, 1647, 1441, 1229, 1156, 1074, 857 |
| C | 2940, 2861, 2115s, 1733, 1610, 1438, 1362, 1263, 1073, 984 |
| D | 2943, 2862, 2123s, 1679s, 1604s, 1520, 1443, 1244, 1167, 852, 835 |
| E | 2942, 2863, 2117s, 1708s, 1645, 1451, 1234s, 1152s, 1088, 1023, 927, 854 |
| F | 2945, 2860, 2119s, 1748s, 1681s, 1443, 1234s, 1153s, 1039, 990 |
| G | 2944, 2860, 2116s, 1740s, 1690s, 1445, 1366, 1238s, 1155s, 1017, 852 |
| H | 2938, 2859, 2115s, 1737s, 1715s, 1445, 1374, 1373, 1229s, 1150s, 1075, 1033, 986 |
| J | 3440 (broad), 2938, 2115s, 1714, 1652s, 1445, 1229s, 1151s, 1089, 1076, 1034, 988. |

[a]s indicates strong

Table IV summarizes nuclear-magnetic resonance (NMR) data obtained from CDCl$_3$ on the new A52688 factors. In the Table, signals are reported relative to TMS (as zero).

TABLE IV

NMR Data on A52688 Factors[a]

| Group | A | C | D | E | F[b] | G[b] | H | J | K |
|---|---|---|---|---|---|---|---|---|---|
| Olefinics | 6.48 | 6.48 | 6.92 | 6.49 | 7.33 | 6.42 | 6.50 | 6.49 | 6.41 |
|  | 6.21 | 6.25 | 6.24 | 6.21 | 6.41 | 6.25 | 6.22 | 6.21 | 6.25 |
|  | 6.06 | 6.06 | 5.74 | 6.11 | 6.24 | 6.18 | 5.98 | 6.13 | 6.17 |
|  | 5.72 |  |  | 5.72 | 6.11 | 6.07 | 5.72 | 5.73 | 6.07 |
|  |  |  |  |  | 5.73 | 5.72 |  |  |  |
| CH—O | 5.07 | 4.24 | 5.09 | 5.06 | 5.08 | 5.07 | 5.08 | 5.08 | 5.06 |
|  | 4.24 | 4.05 |  | 4.21 |  | 4.28 | 5.32 | 4.07 | 4.27 |
|  | 3.69 | 3.69 |  | 3.97 |  |  | 3.88 | 3.86 |  |
| Alkyls | 2.75 | 2.75 | 2.74 | 2.70 | 2.4– | 2.67 | 2.80 | 2.71 | 2.67 |
|  | 2.68 | 2.68 | 1.95 | 2.55 | 2.85 | ~1.5–2.3 | 2.70 | 2.52 | 2.30 |
|  | 2.09 | 2.09 | ~1.66 | 2.00 | ~1.6 |  | 2.15 | 2.04 |  |
|  | 1.95 | 1.5–1.8 |  | 1.80 |  |  | 1.6–2.0 | 1.6–2.0 | 15–22 |
|  | ~1.7 |  |  | ~1.6 |  |  |  |  |  |
| CH$_3$ | 2.19 |  | 2.20 | 2.15 | 2.17 | 2.19 | 2.19 | 2.19 | 0.98 |
|  | 1.91 |  | 1.93 | 1.90 | 2.15 | 2.10 | 2.15 | 1.91 | 0.98 |
|  |  |  |  |  | 1.93 | 1.92 | 1.93 | 3.52 (OCH$_3$) |  |
| OH[c] | 2.24 | 2.20 |  | 2.26 |  |  | 2.47 | 2.38 |  |
|  | 2.24 | 2.20 |  |  |  |  |  |  |  |

[a]Samples run in CDCl$_3$; TMS internal standard.
[b]Sample not completely pure.
[c]Presumed to be due to —OH.

The optical rotations of some of the A52688 factors are summarized in Table V.

TABLE V

Optical Rotations of A52688 Factors

| A52688 Factor | $[\alpha]_{589}^{25}$ | $[\alpha]_{365}^{25}$ | Conc. (mg/ml) | Solvent |
|---|---|---|---|---|
| A | +28.0° | +247.0° | 10 | CHCl$_3$ |
| C | +30.6° |  | 10 | EtOAc:MeOH |
| F | +27.2° |  | 10 | Toluene:MeOH |
| G | +17.2° | +152.4° | 10 | Toluene:MeOH |

Table VI summarizes the mass spectral data for the A52688 factors and the diacetyl derivative of A52688 factor A.

TABLE VI

Mass Spectral Data for A52688 Compounds

| Compound | M+ | Found | Calculated |  |
|---|---|---|---|---|
| Factor A | 396[a] |  |  |  |
| Diacetyl Factor A | 480[a] | 420.20426 | 420.20491 | (C$_{25}$H$_{28}$N$_2$O$_4$)[c] |
| Factor B | 163[a,b] | 163.06339 | 163.06333 | (C$_9$H$_9$NO$_2$) |
| Factor C | 314[a,b] | 314.16304 | 314.16304 | (C$_{18}$H$_{22}$N$_2$O$_3$) |
| Factor D | 376[a,b] | 376.17907 | 376.17869 | (C$_{23}$H$_{24}$N$_2$O$_3$) |
| Factor E | 396[b] |  |  |  |
| Factor F | 436[a,b] | 436.20054 | 436.19982 | (C$_{25}$H$_{28}$N$_2$O$_5$) |
| Factor G | 438[a,b] | 438.21379 | 438.21547 | (C$_{25}$H$_{30}$N$_2$O$_5$) |
| Factor H | 438[a,b] |  |  |  |
| Factor J | 410[a,b] |  |  |  |
| Factor K | 440[b] | 440.23441 | 440.2311 | (C$_{23}$H$_{32}$N$_2$O$_5$) |

[a]Electron Impact
[b]Field Desorption
[c](H—CH$_3$COOH)

A52688 factor C (crystallized from ethyl acetate-toluene) and A52688 factor D (crystallized from toluene-hexane) had the characteristic X-ray powder diffraction patterns presented in Table VII (Cu++ target X-ray, nickel filter, Debye-Scherrer camera 114.6 mm diameter, d=interplanar spacing in angstroms):

TABLE VII

X-Ray Patterns of A52688 Factors C and D

| A52688 Factor | d | Relative Intensity (I/I$_1$) |
|---|---|---|
| C | 6.67 | .36 |
|  | 5.46 | .45 |
|  | 5.09 | 1.00 |
|  | 4.71 | .18b |
|  | 4.31 | .09 |
|  | 4.01 | .36 |
|  | 3.90 | .18 |
|  | 3.65 | .36 |
|  | 3.50 | .18 |
|  | 3.26 | .27 |
|  | 3.04 | .05 |
|  | 2.95 | .05 |
|  | 2.69 | .05 |
| D | 12.90 | .39 |
|  | 8.46 | .11 |
|  | 7.17 | .17 |
|  | 6.61 | .39 |
|  | 5.95 | .97 |
|  | 5.49 | 1.00 |
|  | 5.13 | .58 |
|  | 4.83 | .22 |
|  | 4.42 | .72 |
|  | 4.16 | .28 |
|  | 3.93 | .06 |
|  | 3.87 | .22 |
|  | 3.62 | .11 |
|  | 3.51 | .56 |
|  | 3.21 | .06 |
|  | 3.13 | .08 |
|  | 3.06 | .06 |
|  | 2.81 | .06 |

The individual factors of the A52688 complex can be separated and identified by the use of chromatography. High performance liquid chromatography (HPLC) is especially useful for this purpose.

Two particularly useful analytical HPLC systems for separating the A52688 factors are described in Examples 17 and 18. The retention times (in minutes) of the A52688 factors in these systems are shown in Table VIII.

TABLE VIII

HPLC Retention Times of A52688 Factors in Two Isocratic Solvent Systems

| System | Factor | Retention Time (min.) |
|---|---|---|
| I[a] | A | 8.5 |
|  | B | 2.8 |
|  | C | 3.4 |

TABLE VIII-continued

HPLC Retention Times of A52688 Factors
in Two Isocratic Solvent Systems

| System | Factor | Retention Time (min.) |
|---|---|---|
|  | E | 9.4 |
|  | H | 12.7 |
|  | J | 13.2 |
| II[b] | D | 34.2 |
|  | F | 14.6 |
|  | G | 13.4 |
|  | K | 14.0 |

[a]See Example 17
[b]See Example 18

The organism useful for the preparation of the A52688 antibiotic complex was obtained from the Centraalbureau voor Schimmelcultures Baarn in the Netherlands, where it was given the designation *Mycoleptodiscus terrestris* (Gerdemann) Ostazeski 231.53.

A culture of the A52688-producing organism has also been deposited and made part of the stock culture collection of the Northern Regional Research Center, Agricultural Research, North Central Region, 1815 North University Street, Peoria, Ill., 61604, from which it is available to the public under the accession number NRRL 15601.

As is the case with other organisms, the characteristics of *Mycoleptodiscus terrestris* NRRL 15601 are subject to variation. For example, artificial variants and mutants of the NRRL 15601 strain may be obtained by treatment with various known physical and chemical mutagens, such as ultraviolet rays, X-rays, gamma rays, and N-methyl-N'-nitro-N-nitrosoguanidine. All natural and artificial variants, mutants and recombinants of *Mycoleptodiscus terrestris* NRRL 15601 which retain the characteristic of production of the A52688 antibiotics may be used in this invention.

The A52688 antibiotic complex is prepared by culturing *Mycoleptodiscus terrestris* NRRL 15601, or a mutant or variant thereof which produces these compounds, under submerged aerobic conditions in a suitable culture medium until substantial antibiotic activity is produced.

The A52688-producing culture is easily subcultured to many agar media. Viability on slants is poor after a two- to three-week period. Slants prepared with the slant medium described in Example 1 or potato-dextrose-modified agar (PDA+5 g/L agar, adjusted to pH 6.0), however, will sustain growth for from four to six weeks. A declining culture shows increasingly large vacuoles in the hyphae; a dead culture is virtually hollow.

In flasks, vegetative growth is fragile and does not respond well to vigorous chopping in a microblender.

Slants and vegetative cultures will take several days to show evidence of growth when inoculated from liquid nitrogen cultures due to an unexplained lag phase.

The antibiotic complex is very stable even in broth. When the broth was maintained at pH 5, 7, and 8.5 either overnight at room temperature or for one hour at 55° C. (waterbath), no significant activity loss was detected.

The culture medium used to grow *Mycoleptodiscus terrestris* NRRL 15601 can be any one of a number of media. For economy in production, optimal yield, and ease of product isolation, however, certain culture media are preferred. Thus, for example, preferred carbon sources in large-scale fermentation include carbohydrates such as dextrose, galactose, starch, and glycerol, and oils such as soybean oil. Preferred nitrogen sources include fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of the A52688 antibiotics, submerged aerobic fermentation in tanks is preferred. Small quantities of the A52688 antibiotic may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

*M. terrestris* NRRL 15601 can be grown at temperatures between about 20° and about 32° C. Optimum antibiotic production appears to occur at temperatures of about 25° C.

As is customary in aerobic submerged culture processes, sterile air is bubbled through the culture medium. For efficient antibiotic production the percent of air saturation for tank production should be about 30 or above (at 26° C. and one atmosphere of pressure).

Antibiotic production can be followed during the fermentation by testing samples of the broth against organisms known to be sensitive to these antibiotics. One useful assay organism is *Micrococcus luteus.* In addition, antibiotic production can be monitored by HPLC with UV detection.

Following its production under submerged aerobic fermentation conditions, the A52688 antibiotics can be recovered from the fermentation medium by methods used in the fermentation art. Recovery of the A52688 complex is accomplished by an initial filtration of the fermentation broth. The mycelia can then be extracted, and the mycelial extract can be combined with the filtered broth to be further separated to give the antibiotic complex. A variety of techniques may be used for the separation of the complex. A preferred technique involves adjusting the pH of the mycelial extract/broth mixture to about pH 4 and passing this solution over an adsorbent resin column to give the A52688 complex.

The acyl ester derivatives of A52688 factors A, C, D, E, G, H, J and K can be prepared by treating the factor with an acylating agent using conventional procedures. Suitable organic solvents for this reaction include pyridine and triethylamine.

Typical acylating agents include acyl anhydrides, acyl halides (usually in combination with an acid scavenger), and active esters of organic acids. Acylation can also be achieved by using a mixture of an organic acid and a dehydrating agent such as N,N'-dicyclohexylcarbodiimide. Esterification can be monitored using standard techniques such as thin-layer chromatography (TLC) to determine the time required for the desired reaction. Once formed, the desired ester derivatives can be separated and purified by known techniques.

The A52688 antibiotic complex and the individual A52688 factors inhibit the growth of certain pathogenic organisms. In Table IX the standard discplate-assay activity of the A52688 factors is summarized. Activity is measured as the diameter (in mm) of the observed zone of inhibition; the diameter of the disc used in each case was 6.35 mm.

TABLE IX

Disc-Plate Activity of the A52688 Factors

| Test Organism | Zone Diameters (mm) A52688 Factor[a] | | | | | | | | |
|---|---|---|---|---|---|---|---|---|---|
| | A | B | C | D | E | F | G | H | J | K |
| Staphylococcus aureus | 26 | 25[b] | 16 | 18 | 21 | 26 | 36 | 20 | 23 | 25 |
| Bacillus subtilis | 30 | 21 | 23 | 18 | 29 | 27 | 30 | 16 | 19 | 18 |
| Micrococcus luteus | 36 | 22 | 33 | 26 | 24 | 30 | 32 | 27 | 29 | 29 |
| Mycobacterium avium | 14 | —[c] | 18 | 13 | 15 | 17[b] | 10 | 10 | 14 | 11 |
| Saccharomyces pastorianus | 20 | 14[b] | 15[b] | 13 | 20 | 22[b] | 24 | 16 | 19 | 20 |
| Neurospora crassa | 39 | 24 | 22 | 22 | 34 | 33 | 41 | 33 | 36 | 37 |
| Candida albicans | 33 | 11 | 16 | 19 | 29 | 21 | 35 | 18 | 22 | 20 |
| Trichophyton mentagroprophytes | 45 | 19 | 15 | 21 | 43 | 20 | 44 | 35 | 37 | 32 |
| Proteus vulgaris | 24[b] | — | 26[b] | 12 | 21[b] | 20[b] | 27[b] | 17 | 22 | 19 |
| Salmonella gallinarium | 21 | — | 38 | 14 | 19 | 11 | 23 | 16 | 17 | 17 |
| Escherichia coli | 24 | — | 24 | 15 | 18 | 17 | 20 | 15 | 15 | |
| Pseudomonas aeruginosa | 23 | — | tr[d] | 13 | 17 | tr | 23 | 11 | 12 | 11 |
| Serratia marcescens | 20 | — | 15[b] | 12 | 17 | tr | 17 | 10 | 12 | 11 |
| Pseudomonas solanacearum | 26 | — | 20 | 17 | 24 | 10[b] | 31 | 18 | 21 | 19 |
| Escherichia coli[e] | 20 | — | 20 | 11 | 16 | tr | 18 | 10 | 13 | 11 |
| Bacillus stereothermophilus | 35 | 21 | 35 | 21 | 30 | 27 | 33 | 24 | 25 | 25 |

[a]Conc = 0.1 mg/ml;
[b]overgrowth;
[c]inactive;
[d]trace;
[e]in minimal medium

A52688 factors A, C, D, E, F, G, H, J and K and the specified acyl esters of factors A, C, D, E, G, H, J and K are especially useful as oncolytic agents. In tests in mice, for example, representative A52688 factor A inhibited the growth of a number of tumor systems, including adenocarcinoma 755, plasma cell myeloma X-5563, lymphosarcoma 6L3 HED, Lewis lung tumor, solid leukemia P1534J and ovarian M-5 tumor.

Table X summarizes the results of experiments in which mice bearing the murine-transplanted tumor adenocarcinoma 755 were treated with compounds of this invention. In each test the compound was administered by the intraperitoneal route at specified dose levels. The compound was administered over a ten-day period, either on a daily basis or on days one, five and nine, as indicated.

TABLE X

Activity of A52688 Factors vs. Adenocarcinoma 755 in Mice

| A52688 Factor | Dose Level (mg/kg) | Percent Tumor Inhibition | Toxic Deaths | No. of Mice Tested | Dosage Schedule |
|---|---|---|---|---|---|
| A | 0.40 | 91 | 6 | 9 | Daily for 10 days |
| | 0.35 | 69 | 1 | 10 | Daily for 10 days |
| | 0.30 | 55 | 1 | 10 | Daily for 10 days |
| | 0.25 | 3 | 0 | 10 | Daily for 10 days |
| C | 0.50 | 72 | 5 | 10 | Daily for 10 days |
| | 0.25 | 47 | 0 | 10 | Daily for 10 days |
| | 0.125 | 60 | 0 | 10 | Daily for 10 days |
| E | 1.00 | toxic | 10 | 10 | Daily for 10 days |
| | 0.50 | 74 | 3 | 8 | Daily for 10 days |
| | 0.25 | 22 | 0 | 9 | Daily for 10 days |
| F | 2.00 | toxic | 10 | 10 | Daily for 10 days |
| | 1.00 | 91 | 2 | 9 | Daily for 10 days |
| | 0.50 | 69 | 0 | 10 | Daily for 10 days |
| | 0.25 | 51 | 0 | 10 | Daily for 10 days |
| G | 2.80 | toxic | 10 | 10 | days 1, 5 and 9 |
| | 2.00 | 60 | 7 | 10 | days 1, 5 and 9 |
| | 1.40 | 72 | 6 | 10 | days 1, 5 and 9 |
| | 1.00 | 54 | 1 | 10 | days 1, 5 and 9 |
| | 0.70 | 20 | 0 | 10 | days 1, 5 and 9 |
| | 0.50 | 10 | 0 | 10 | days 1, 5 and 9 |

Table XI summarizes acute toxicity data on the various A52688 factors in mice.

TABLE XI

Acute Toxicity of A52688 Factors in Mice

| Factor[a] | Intraperitoneal[b] LD$_{50}$ (mg/kg) | Oral[b] LD$_{50}$ (mg/kg) |
|---|---|---|
| A | 3.125 | 8.84 |
| B | >75. | |
| C | <2.34 | |
| D | 0.992 | |
| E | 3.54 | |
| F | 5.00 | |
| G | 7.94 | |

[a]Compounds formulated in aqueous PVP
[b]Route test compound administered

When using the novel compounds of this invention as antibacterial and/or antineoplastic agents in mammals, compositions containing the compounds are administered parenterally. Such compositions comprise a compound of formula 1 together with a suitable vehicle. Compositions may be formulated for parenteral administration by methods recognized in the pharmaceutical art.

Effective injectable compositions containing these compounds may be in either suspension or solution form. In the solution form the compound is dissolved in a physiologically acceptable vehicle. Such vehicles comprise a suitable solvent, preservatives such as benzyl alcohol, if needed, and buffers.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

The doses which are effective to control infections and/or treat neoplasms will vary with a number of factors, such as the severity of the infection and/or neoplasm and the age, weight, and condition of the animal. In treating infections, the amount in mg/kg which is effective to treat infections in test animals can be adjusted on a weight basis to treat higher animals. In treating neoplasms, however, it is recognized that total body surface of the animal must be taken into account when determining dosage levels.

It is also recognized in the art that different treatment regimes may be used. The choice of regime will depend on a variety of factors such as, for example, the target infection or tumor, the animal being treated, etc.

In order to illustrate more fully the operation of this invention, the following examples are provided:

EXAMPLE 1

A. Shake-Flask Fermentation of A52688

A culture of *Mycoleptodiscus terrestris* NRRL 15601 is prepared and maintained on an agar slant having the following composition:

| Ingredient | Percent[a] |
|---|---|
| Glucose | 0.5 |
| Galactose | 0.5 |
| Glycerol | 0.5 |
| Soluble starch | 0.5 |
| Yeast extract | 0.5 |
| Dog Chow[b] | 0.5 |
| $KH_2PO_4$ | 0.3 |
| $MgSO_4.7H_2O$ | 0.05 |
| $FeSO_4.7H_2O$ | 0.01 |
| $CaCO_3$ | 0.1 |
| $MnCl_2.4H_2O$ | 0.005 |
| $ZnSO_4.7H_2O$ | 0.005 |
| Agar | 2.0 |
| Tap water added to a volume of 1000 ml | |

[a]weight/volume
[b]Ralston Purina, St. Louis, MO

Presterilization pH=5.6
Adjust pH to 5.0 with HCl
Poststerilization pH: unknown

The inoculated slants are incubated at 25° C. for 7 days. A mature slant culture is used to inoculate 50 ml of a vegetative medium having the following composition:

| Ingredient | Percent[a] |
|---|---|
| Glucose | 0.25 |
| Galactose | 0.25 |
| Glycerol | 0.25 |
| Soluble starch | 0.25 |
| Yeast extract | 0.25 |
| Fish meal[b] | 0.25 |
| Mannose | 0.25 |
| Lactose | 0.25 |
| Maltose | 0.25 |
| Soybean oil | 0.25 |
| Corn oil | 0.25 |
| $KH_2PO_4$ | 0.3 |
| $MgSO_4.7H_2O$ | 0.05 |
| $MnCl.4H_2O$ | 0.005 |
| $ZnSO_4.7H_2O$ | 0.005 |
| $FeSO_4.7H_2O$ | 0.002 |
| Tap water added to a volume of 1000 ml | |

[a]weight/volume except for oils which were volume/volume
[b]Seacoast Products Co., Portmonouth, NJ Presterilization pH=5.6
Adjust pH to 6.0–6.5 with NaOH
Poststerilization pH=5.6

The inoculated vegetative medium is incubated in a 250 ml wide-mouth Erlenmeyer flask at 25° C. on a rotary shaker (250 RPM, 5-cm diameter circle) for 96 hours. At 42 and 96 hours, the culture medium is blended for 10 seconds in a blender (Waring).

This incubated vegetative medium may be used directly to inoculate the second-stage vegetative medium. Alternatively and preferably, it can be stored for later use by maintaining the culture in the vapor phase of liquid nitrogen in ampoules prepared from the vegetative culture after 96 hours by methods known in the art.

A liquid-nitrogen ampoule thus prepared (0.5 ml) is used to inoculate 50 ml of a first-stage vegetative medium having the following composition:

| Ingredient | Percent[a] |
|---|---|
| Sucrose | 3.0 |
| Defatted cottonseed flour[b] | 0.5 |
| $FeSO_4.7H_2O$ | 0.01 |
| $K_2HPO_4$ | 0.1 |
| $MgSO_4.7H_2O$ | 0.05 |
| $NaNO_3$ | 0.05 |
| KCl | 0.05 |
| Czapek's mineral stock[c] | 0.2 |
| Deionized water to a volume of 1000 ml | |

[a]weight/volume except for Czapek's solution which is volume/volume
[b]Proflo, Traders Oil Mill Co.
[c]Czapek's mineral stock solution:

| Ingredient | Percent (w/v) |
|---|---|
| KCl | 10. |
| $MgSO_4.7H_2O$ | 10. |
| $FeSO_4.7H_2O$ | .2 |
| Deionized water to a volume of 1000 ml | |

Presterilization pH: 7.4
Poststerilization pH: 6.4

The inoculated first-stage vegetative medium is incubated in a 250 ml wide-mouth Erlenmeyer flask at 25° C. for 72 hours on a rotary shaker (250 RPM, 5-cm diameter stroke). The first stage culture is blended in a blender for 10 seconds at 42 and 66 hours.

B. Tank Fermentation of A52688

In order to provide a larger volume of inoculum, 10 ml of the incubated first-stage vegetative medium is used to inoculate 400 ml of a second-stage vegetative medium having the same composition as that of the first stage. The second-stage medium is incubated in a 2-liter wide-mouth Erlenmeyer flask at 25° C. for 48 hours on a rotary shaker (250 RPM, 5-cm diameter stroke).

Incubated second-stage vegetative medium (800 ml) is used to inoculate 100 liters of sterile production medium having the following composition:

| Ingredient | Percent[a] |
|---|---|
| Soluble starch | 1.0 |
| Glucose | 4.0 |
| Fish meal[b] | 1.0 |
| CaCO$_3$ | .5 |
| Tween 80 | .1 |
| Tap water to a volume of 1000 ml | |

[a]weight/volume except for Tween 80, which is volume/volume
[b]Seacoast

Presterilization pH: 6.5
Poststerilization pH: 6.9

The inoculated production medium is allowed to ferment in a 165-liter fermentation tank at a temperature of 27° C. for about 114 to 138 hours. The fermentation medium is aerated with sterile air at the rate of 0.125 v/v/m and is stirred with conventional agitators at 150 RPM. Polypropylene glycol (MW=2,000) is used as an antifoam agent.

EXAMPLE 2

Procedure 1

Whole fermentation broth (164 L) was filtered using a filter aid (Hyflo Super-Cel). The mycelial cake was then extracted twice with methanol (30 L each time) in a press. The extracts were combined and concentrated under vacuum to an aqueous solution (15 L) which was then combined with the filtered broth (165 L). The pH of this combined solution was adjusted to 4.0 with hydrochloric acid, and the acidified solution was applied to a column containing 15 L of Diaion HP-20 (Mitsubishi Chemical Industries, Ltd., Tokyo, Japan) at a flow rate of 200 ml/minute. The column was washed with water (30 L) and methanol:water (1:4, 30 L) and then was eluted with methanol, collecting 4-L fractions. Each fraction was analyzed for biological activity using paper discs on agar plates seeded with *Micrococcus luteus*, *Pseudomonas solanacearum*, or *Neurospora crassa*. Fractions 4–33 were combined and concentrated under reduced pressure to a volume of 1.8 L. This solution contained 135 g of solids, of which approximately 12 g were A52688 complex.

Procedure 2

Whole fermentation broth (210 L) was filtered using a filter aid (Hyflo Super-Cel). The mycelial cake was then extracted twice with methanol (35 L each time) in a press. The filtered broth was discarded. The methanol extracts were combined and concentrated under vacuum to an aqueous solution which then was diluted to a volume of 70 L with deionized water. The pH of this solution was adjusted to 4.0 with hydrochloric acid, and Dianion HP-20 resin (7 L) was added. The mixture was stirred for one hour, and the resin effluent was separated by filtration. The resin was washed with water (14 L) and then was eluted with acetonitrile (30 L and then 48 L). The eluates were combined and concentrated under reduced pressure to a volume of 8 L. This solution contained about 218 g of total solids, of which 95 g were A52688 complex. Biological activity was monitored using a paper disc assay on agar plates seeded with *Bacillus subtilis*.

EXAMPLE 3

Separation of Factors from the A52688 Complex

A portion of the concentrate containing the A52688 complex (1 L, which contained about 75 g of solids) was dried onto silica gel (500 ml, Grade 62, 60–200 mesh, MCB Reagents, supplied by Curtin Matheson Scientific, Inc., Elk Grove Village, Ill.). This was applied to a 4"×120" glass column packed with silica gel (15 L, Grade 62) in toluene:ethyl acetate (4:1). The column was developed with toluene:ethyl acetate (150 L of 4:1; 60 L of 1:1; and 75 L of 1:4) at a flow rate of 200 ml/min. collecting 4-L fractions. Biological activity of the fractions was monitored by agar-disc assay, using *Micrococcus luteus*. Factor composition was monitored by thin layer chromatography (TLC), using silica gel 60 plates without fluorescent indicator (E. Merck). The plates were developed using chloroform:methanol (9:1); factors were detected by bioautography with *M. luteus*.

Fractions were combined as shown in Table XII.

TABLE XII

Column Separation of the A52688 Factors on Silica Gel

| Fractions | Factors | Concentrate Volume (ml) | Solids (g) |
|---|---|---|---|
| 6–8 | D, F | 300 | .18 |
| 12–15 | D, F + unknown | 500 | .25 |
| 16–19 | A, B[a], G[b](H, J, K)[c] | 550 | 3.14 |
| 20–26 | G | 820 | .41 |
| 41–43 | A, B[a,b], G | 200 | .98 |
| 44–58 | A[b], B[a], G | 650 | 1.24 |
| 66–72 | A, B[a], C[b], G | 730 | .51 |

[a]It was later found that factors B and E have the same $R_f$ value in the TLC system used, thus factor E could also be present
[b]Major component
[c]These factors were isolated later by HPLC methods; they did not separate from factor G by TLC Each group of fractions was concentrated to the volume shown in the table in preparation for final purification of the major component of each.

EXAMPLE 4

Purification of A52688 Factor A

The concentrate from fractions 44–58 from Example 3 was dried onto approximately 50 ml of silica gel (Grade 62) under vacuum. The sample was applied to a 4.0-x 65-cm glass column packed with 550 ml of silica gel (Grade 62) in toluene-ethyl acetate (7:3). The column was developed with the same solvent (8.75 L) at a flow rate of 25 ml/min, collecting 25-ml fractions. Biological activity of the fractions was monitored by disc assay with *M. luteus*. Factor composition of the active fractions was monitored by TLC as described in Example 3.

Fractions 97–210, which contained only Factor A, were combined and concentrated to an oily residue. This was crystallized from ethyl acetate (ca. 100 ml)/toluene to give 349 mg of A52688 factor A. A second crop was obtained to give an additional 171 mg of factor A.

EXAMPLE 5

Purification of A52688 Factor B

The concentrate from fractions 41–43 from Example 3 was dried onto approximately 50 ml of silica gel (Grade 62). The sample was applied to a 4.0-x 65-cm glass column packed with 500 ml of silica gel (Grade 62) in toluene:ethyl acetate (3:1). The column was developed with 11 L of the same solvent at a flow rate of 25 ml/min, collecting 25-ml fractions. Factor composition was monitored as described in Example 3.

Fractions 111–145 were combined and concentrated to an oily residue. This was crystallized from ethyl acetate (ca. 40 ml)/toluene to give 71 mg of A52688 factor B.

EXAMPLE 6

Purification of A52688 Factor C

The concentrate from fractions 66–72 from Example 3 was dried onto approximately 20 ml of silica gel (Grade 62) and applied to a 2.3-x 50-cm glass column filled with 200 ml of silica gel (Grade 62) in toluene-:ethyl acetate (3:2). The column was developed with 5.2 L of the same solvent at a flow rate of 4.2 ml/min, collecting 17-ml fractions. Factor composition was monitored as described in Example 3.

Fractions 173–310 were combined and concentrated to an oily residue. This was crystallized from ethyl acetate/toluene to give 52.5 mg of A52688 factor C.

EXAMPLE 7

Purification of A52688 Factor D

Concentrates from fractions containing factors D and F, obtained as described in Example 3, were combined. A portion of this combined concentrate (285 ml=200 mg solids) was further concentrated to an oil. The oil was dissolved in 3 ml of hexane:ethyl acetate (85:15). This solution was applied to a 2.3-x 50-cm glass column packed with 180 ml of silica gel (Woelm, 63–200 micron, Activity III, Universal Scientific Inc., Atlanta, Ga.). The column was prepared and developed with hexane:ethyl acetate (3.7 L, 85:15) at a flow rate of 16 ml/min, collecting 16-ml fractions. Factor composition was monitored as described in Example 3, except that the TLC solvent system was chloroform:methanol (95:5).

Fractions 34–84 were combined and concentrated to an oil. The product was crystallized from toluene-hexane to give 7.4 mg (first crop) and 5.0 mg (second crop) of A52688 factor D.

EXAMPLE 8

Purification of A52688 Factor E

A concentrate containing 1.3 g of solids from a column purification similar to that described in Example 3 was further concentrated to an oil. The oil was dissolved in toluene:ethyl acetate (30 ml, 4:1). This solution was applied to a 4.6-x 65-cm glass column packed with 700 ml of silica gel (Woelm) in toluene: ethyl acetate (4:1). The column was developed with 10.4 L of the same solvent at a flow rate of 40 ml/min, collecting 160-ml fractions. Factor composition was monitored as described in Example 7.

Fractions 24–48 were combined and concentrated to an oil. Factor E was crystallized from ethyl acetate/toluene. Three crops of crystals were obtained: 52 mg (100% A52688E); 103 mg (80% A52688E, 11% A52688B, 9% impurities); and 29 mg (98% A52688E, 2% A52688B). Purity was measured by analytical HPLC, using the system described in Example 15.

EXAMPLE 9

Purification of A52688 Factor F

The remainder of the combined concentrate containing factors D and F which was discussed in Example 7 was concentrated to an oil (containing 500 mg solids). This oil was dissolved in hexane:ethyl acetate (85:15, 20 ml) and applied to a 4.0-×65-cm glass column packed with 500 ml of silica gel (Woelm) in hexane:ethyl acetate (85:15). The column was developed with 11.2 L of this solvent at a flow rate of 40 ml/min, collecting 160-ml fractions. Factor composition was monitored as described in Example 7.

Fractions 11–16 were combined and concentrated to an oil. Factor F crystallized from toluene/hexane to give a first crop (45.8 mg), which was a mixture of factors D and F, and a second crop (13.8 mg), which was A52688 factor F.

EXAMPLE 10

Purification of A52688 Factor G

Concentrate in which factor G was the major factor was obtained as described in Example 3. This was further concentrated to an oil, which was dissolved in hexane:ethyl acetate (85:15, 50 ml). This solution was applied to a 4.6-x 65-cm glass column packed with 800 ml of silica gel (Woelm) in hexane:ethyl acetate (85:15). The column was developed with 12.5 L of the same solvent at a flow rate of 25 ml/min, collecting 25-ml fractions. Biological activity of the fractions was monitored as described in Example 3. Factor composition was determined by analytical HPLC as described in Example 16.

Fractions 276–425 were combined and concentrated to an oil. This was crystallized from toluene/hexane to give 2.15 g (first crop) and 257 mg (second crop) of A52688 factor G.

EXAMPLE 11

Purification of A52688 Factor H

A52688 concentrate was separated on a silica gel column as described in Example 3 to give the combined fractions from which factor G was crystallized. The mother liquor from the crystallization contained approximately 57 g of active material in 92 g of total solids. This mother liquor (500 ml) was applied to a 4"-X 120"-glass column packed with 15 L. of silica gel (Grade 62) in hexane:ethyl acetate (4:1). The column was run at a flow rate of 200 ml/min, and 4-L. fractions were collected. Fractions were monitored by disk-assays using *Micrococcus luteus* and by analytical HPLC. The factors were concentrated as follows:

| Fraction No. | Concentrate Volume (ml) | Solids in Concentrate (g) | Factors in Concentrate |
|---|---|---|---|
| 13–16 | 930 | 14.3 | G, H, J, K |
| 18–23 | 1000 | 28.8 | G, H, K |
| 24–32 | 970 | 20.5 | G, H, unknown |

A portion of a pool equivalent to that from fractions 18–23 and obtained from a similar silica-gel column (520-mg solids) was concentrated to an oil. This oil was dissolved in 4 ml of MeOH:CH$_3$CN:H$_2$O (43:43:14) and applied to a glass column packed with 650 ml of Lichroprep RP-18 (25–40 micron). The column was eluted with MeOH:CH$_3$CN:H$_2$O (35:35:30) at a flow rate of 14 ml/min, collecting 21-ml fractions. Detection was by UV absorbance at 254 nm, and fractions were monitored by analytical HPLC. Fractions 95–120 were combined, concentrated and lyophilized to give 128 mg of factor H.

EXAMPLE 12

Purification of A52688 Factor J

Fractions 13–16 from the first silica-gel column described in Example 11 were concentrated to an oil, which was dissolved in a small amount of toluene and hexane. After this solution was refrigerated, factor G (3.74 g) crystallized. A portion of the mother liquor from this crystallization (16 ml=975 mg solids) was dissolved in MeOH:CH$_3$CN:H$_2$O (4 ml; 43:43:14) and applied to a glass column packed with 650 ml of Lichroprep RP-18 resin (25–40 micron). The column was eluted with MeOH:CH$_3$CN:H$_2$O (35:35:30) at 14 ml/min, collecting 21-ml fractions. Fractions were monitored by analytical HPLC (see Example 17), and those containing factor J were combined, concentrated and lyophilized to give a total of 36.1 mg of factor J.

EXAMPLE 13

Purification of A52688 Factor K

Combined fractions (460-mg solids) containing factors G, H, J and K, obtained as described in Example 11, were purified using an RP-18 column purification as described in Example 12. Fractions from the RP-18 column were concentrated and lyophilized to give 107 mg of material that was a mixture of factors G and K. This preparation was combined with several similar preparations (165-mg total). This was dissolved in 4.5 ml of MeOH:CH$_3$CN:H$_2$O (9:9:7) and applied to a glass column packed with 160 ml of Lichroprep RP-18 (25–40 micron). The column was eluted with MeOH:CH$_3$CN:H$_2$O (8:8:9) at a flow rate of 6.5 ml/min., collecting 10-ml fractions. Fractions were monitored by analytical HPLC. Fractions having the desired activity were combined, concentrated and lyophilized to give 14.4 mg of factor K. Since factor K absorbs moisture readily, it is held in solution in methanol.

EXAMPLE 14

Analytical HPLC—Gradient System

The following gradient system was used for separating some of the A52688 factors:
Column: 4.6-x 250-mm, stainless steel
Packing: Ultrasphere ODS 5 micron (prepacked by Altex Scientific, Inc., division of Beckman Instruments Inc., Berkeley, Calif.)
Column Temp: ambient
Solvent A: Methanol:acetonitrile:water (2:1:2)
Solvent B: Methanol:acetonitrile:water (1:8:1)
Gradient: Linear gradient from 0 to 80% solvent B to solvent A in the first 25 minutes; remain at 80% B until 30 min.; return to 0% B by 35 min.; re-equilibrate at 0% B until 40 min.
Flow Rate: 1.0 ml/min.
Detection: UV at 285 nm [Spectromonitor III, Laboratory Data Control (LDC), division of Milton Roy Inc., Riviera Beach, Fla.]
System Control: Chromatograph Control Module (LDC)
Pumps: Constametric III (LDC)
Injector: Rheodyne Model 7126 valve

| Factor | Retention Time (min.) |
|---|---|
| A | 17.6 |
| B | 3.0 |
| C | 5.2 |
| D | 25.9 |
| E | 19.2 |
| F | 21.3 |

Factor G does not separate from factor E in this HPLC system. Also, differences in UV absorption maxima between two groups of factors (A, B, C, E, H and J and D, F, G and K) make quantitation of complex mixtures difficult when one wavelength is used. For complete separation of factors, therefore, two separate isocratic analytical HPLC systems should be used (see Examples 15, 16, 17 and 18).

EXAMPLE 15

Analytical HPLC—Isocratic System I

Column: 4.6-x 250-mm, stainless steel
Packing: Shandon ODS Hypersil-5 micron (Shandon Southern Instruments, Inc., Sewickley, Pa.)
Column Temp: ambient
Solvent A: Methanol:acetonitrile:water (2:1:2)
Solvent B: Methanol:acetonitrile:water (1:8:1)
Isocratic: 20% solvent B to solvent A to give methanol:acetonitrile:water (34:32:34)
Flow Rate: 1.0 ml/min.
Detection: UV at 285 nm (Spectromonitor III)
Pumps: Constametric III (LDC)
Injector: Rheodyne Model 7126 valve
System Control: Chromatograph Control Module (LDC)

| Sample: Factor | Retention Time (min.) |
|---|---|
| A | 13.8 |
| B | 3.1 |
| C | 3.7 |
| E | 15.9 |

EXAMPLE 16

Analytical HPLC—Isocratic System II

Column: 4.6-x 250-mm, stainless steel
Packing: Ultrasphere ODS-5 micron (prepacked by Altex Scientific Inc.)
Solvent A: Methanol:acetonitrile:water (2:1:2)
Solvent B: Methanol:acetonitrile:water (1:8:1)
Isocratic: 60% solvent B to solvent A to give methanol:acetonitrile:water (22:56:22)
Flow Rate: 1.0 ml/min.
Detection: UV at 254 nm (Spectromonitor III)
Pumps: Constametric III (LDC)
Injector: Rheodyne Model 7126
System Control: Chromatograph Control Module (LDC)

| Sample: Factor | Retention Time (min.) |
|---|---|
| D | 12.1 |
| F | 8.1 |
| G | 6.6 |

*Although the UV maximum for factor D is 330 nm, it can be detected at 254 nm except that the extinction coefficient is much less than those of factors F and G.

EXAMPLE 17

Analytical HPLC—Isocratic System III

Column: 4.6-x 250-nm
Packing: Ultrasphere ODS-5 micron
Solvent: Methanol:1% Ammonium acetate in water (4:1)
Flow Rate: 1.0 ml/min.
Detection: UV at 285 nm (LDC Spectromonitor III)
Pumps: Constametric III (LDC)
Injector: Rheodyne Model 7126
System Control: Chromatograph Control Module (LDC)

| Sample: Factor | Retention Time (min.) |
|---|---|
| A | 8.5 |
| B | 2.8 |
| C | 3.4 |
| E | 9.4 |
| H | 12.7 |
| J | 13.2 |

EXAMPLE 18

Analytical HPLC—Isocratic System IV

Column: 4.6-x 250-mm
Packing: Ultrasphere ODS-5 micron
Solvent: Methanol: 1% Ammonium acetate in water (3:1)
Flow Rate: 1.0 ml/min.
Detection: UV at 254 nm (LDC Spectromonitor III)
Pumps: Constametric III (LDC)
Injector: Rheodyne Model 7126
System Control: Chromatograph Control Module (LDC)

| Sample: Factor | Retention Time (min.) |
|---|---|
| D | 34.2 |
| F | 14.6 |
| G | 13.4 |
| K | 14.0 |

We claim:
1. A52688 factor A which has the formula

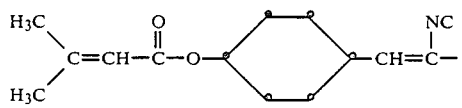

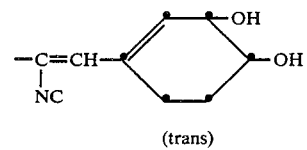
(trans)

and the $C_2$–$C_{18}$-acyl ester derivatives of A52688 factor A.

2. A52688 factor C which has the formula

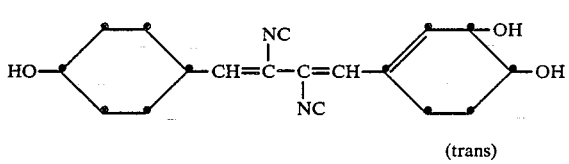
(trans)

and the $C_2$–$C_{18}$-acyl ester derivatives of A52688 factor C.

3. A52688 factor D which has the formula

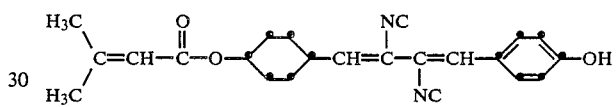

and the $C_2$–$C_{18}$-acyl ester derivatives of A52688 factor D.

4. A52688 Factor E which has the formula

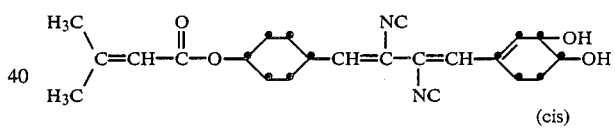
(cis)

and the $C_2$–$C_{18}$-acyl ester derivatives of A52688 factor E.

5. A52688 factor F which has the formula

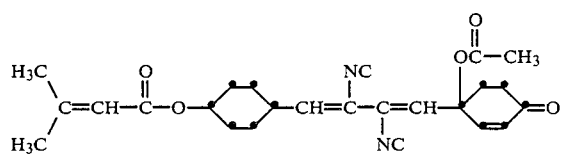

6. A52688 factor G which has the formula

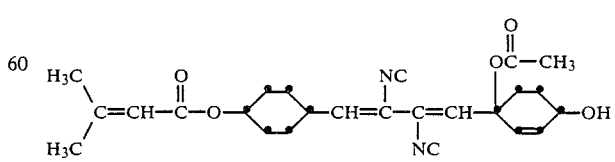

and the $C_2$–$C_{18}$-acyl ester derivatives of A52688 factor G.

7. A52688 factor H which has the formula

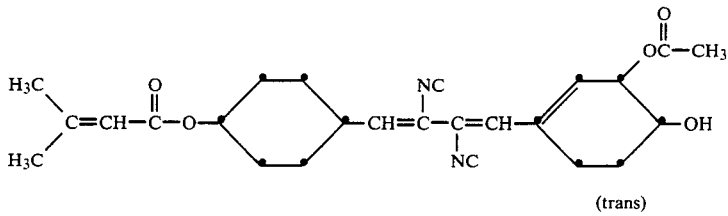

(trans)

and the $C_2$-$C_{18}$-acyl ester derivatives of A52688 factor H.

8. A52688 factor J which has the formula

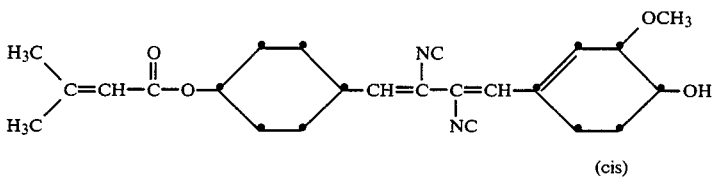

(cis)

and the $C_2$-$C_{18}$-acyl ester derivatives of A52688 factor J.

9. A52688 factor K which has the formula

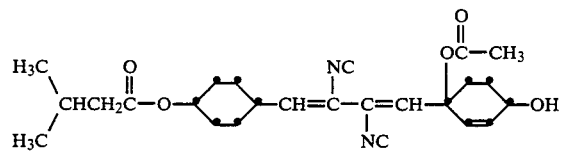

and the $C_2$-$C_{18}$-acyl ester derivatives of A52688 factor K.

10. The method of producing the A52688 antibiotic complex comprising A52688 factors A, C, D, E, F, G, H, J and K which comprises cultivating *Mycoleptodiscus terrestris* NRRL 15601 or an A52688-producing mutant thereof in a culture medium containing assimilable sources of carbon, nitrogen and inorganic salts under submerged aerobic fermentation conditions until a substantial amount of A52688 complex is produced.

11. The method of claim 10 which includes the additional step of separating the A52688 complex from the culture medium.

12. The method of claim 11 which includes the additional step of isolating A52688 factor A from the separated complex.

13. The method of claim 11 which includes the additional step of isolating A52688 factor B from the separated complex.

14. The method of claim 11 which includes the additional step of isolating A52688 factor C from the separated complex.

15. The method of claim 11 which includes the additional step of isolating A52688 factor D from the separated complex.

16. The method of claim 11 which includes the additional step of isolating A52688 factor E from the separated complex.

17. The method of claim 11 which includes the additional step of isolating A52688 factor F from the separated complex.

18. The method of claim 11 which includes the additional step of isolating A52688 factor G from the separated complex.

19. The method of claim 11 which includes the additional step of isolating A52688 factor H from the separated complex.

20. The method of claim 11 which includes the additional step of isolating A52688 factor J from the separated complex.

21. The method of claim 11 which includes the additional step of isolating A52688 factor K from the separated complex.

22. The method of claim 10 in which *M. terrestris* NRRL 15601 is used.

23. An antineoplastic composition which comprises an effective amount of a compound of claim 1 and a suitable vehicle.

24. An antineoplastic composition which comprises an effective amount of a compound of claim 2 and a suitable vehicle.

25. An antineoplastic composition which comprises an effective amount of a compound of claim 3 and a suitable vehicle.

26. An antineoplastic composition which comprises an effective amount of a compound of claim 4 and a suitable vehicle.

27. An antineoplastic composition which comprises an effective amount of a compound of claim 5 and a suitable vehicle.

28. An antineoplastic composition which comprises an effective amount of a compound of claim 6 and a suitable vehicle.

29. An antineoplastic composition which comprises an effective amount of a compound of claim 7 and a suitable vehicle.

30. An antineoplastic composition which comprises an effective amount of a compound of claim 8 and a suitable vehicle.

31. An antineoplastic composition which comprises an effective amount of a compound of claim 10 and a suitable vehicle.

32. A method of inhibiting the growth of neoplasms in mammals which comprises administering parenterally to the mammal an effective amount of a composition of claim 23.

33. A method of inhibiting the growth of neoplasms in mammals which comprises administering parenterally to the mammal an effective amount of a composition of claim 24.

34. A method of inhibiting the growth of neoplasms in mammals which comprises administering parenterally to the mammal an effective amount of a composition of claim 25.

35. A method of inhibiting the growth of neoplasms in mammals which comprises administering parenterally to the mammal an effective amount of a composition of claim 26.

36. A method of inhibiting the growth of neoplasms in mammals which comprises administering parenterally to the mammal an effective amount of a composition of claim 27.

37. A method of inhibiting the growth of neoplasms in mammals which comprises administering parenterally to the mammal an effective amount of a composition of claim 28.

38. A method of inhibiting the growth of neoplasms in mammals which comprises administering parenterally to the mammal an effective amount of a composition of claim 29.

39. A method of inhibiting the growth of neoplasms in mammals which comprises administering parenterally to the mammal an effective amount of a composition of claim 30.

40. A method of inhibiting the growth of neoplasms in mammals which comprises administering parenterally to the mammal an effective amount of a composition of claim 31.

* * * * *

UNITED STATES PATENT AND TRADEMARK OFFICE
CERTIFICATE OF CORRECTION

PATENT NO. : 4,537,777
DATED : August 27, 1985
INVENTOR(S) : Marie T. Anderson, Karl H. Michel and Thomas H. Sands It is certified that error appears in the above—identified patent and that said Letters Patent is hereby corrected as shown below:

Column 22, line 57, "claim 10" should read -- claim 9 --.

Signed and Sealed this

First Day of April 1986

[SEAL]

Attest:

Attesting Officer

DONALD J. QUIGG

Commissioner of Patents and Trademarks